(12) United States Patent
Amir

(10) Patent No.: US 6,269,499 B1
(45) Date of Patent: Aug. 7, 2001

(54) MULTI-AXIS PLANAR MECHANISM FOR A POSITIONER PATIENT PLATFORM

(75) Inventor: Yosef Amir, Glendale, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/342,986

(22) Filed: Jun. 29, 1999

(51) Int. Cl.⁷ .............................. A61G 13/00; A61B 6/04
(52) U.S. Cl. ........................ 5/600; 5/608; 5/611; 5/601
(58) Field of Search .............................. 5/600, 601, 607, 5/608, 610, 611, 11

(56) References Cited

U.S. PATENT DOCUMENTS

| | | | | |
|---|---|---|---|---|
| 3,393,004 | * | 7/1968 | Williams | 5/610 X |
| 3,845,946 | * | 11/1974 | Warden et al. | 5/600 |
| 3,900,906 | * | 8/1975 | Berthelsen | 5/608 |
| 4,572,493 | * | 2/1986 | Hubert | 5/610 X |
| 4,576,368 | * | 3/1986 | Ogawa et al. | 5/601 X |
| 4,958,817 | * | 9/1990 | Heller et al. | 5/607 |
| 5,398,356 | * | 3/1995 | Pfleger | 5/608 |
| 5,528,782 | * | 6/1996 | Pfeuffer et al. | 5/608 X |
| 5,572,567 | | 11/1996 | Khutoryansky et al. | 378/197 |
| 5,621,933 | * | 4/1997 | Knapp et al. | 5/607 X |
| 5,636,259 | | 6/1997 | Khutoryansky et al. | 378/197 |
| 5,657,498 | * | 8/1997 | Hum | 5/601 |
| 5,680,430 | | 10/1997 | Khutoryansky et al. | 378/109 |
| 5,734,694 | | 3/1998 | Khutoryansky et al. | 378/197 |
| 5,751,788 | | 5/1998 | Khutoryansky et al. | 378/197 |
| 5,768,336 | | 6/1998 | Khutoryansky et al. | 378/116 |

FOREIGN PATENT DOCUMENTS

| | | | | |
|---|---|---|---|---|
| 1960444 | * | 9/1970 | (DE) | 5/611 |
| 1903929 | * | 9/1978 | (DE) | 5/610 |
| 2419068 | * | 10/1979 | (FR) | 5/610 |
| 2816564 | * | 10/1979 | (DE) | 5/611 |

\* cited by examiner

*Primary Examiner*—Anthony Knight
*Assistant Examiner*—Robert G. Santos
(74) *Attorney, Agent, or Firm*—McAndrews, Held & Malloy, Ltd.; Christian G. Cabou

(57) ABSTRACT

A multi-axis positioner patient platform comprises a patient table and a base. A first actuator drive has a first end is connected to the patient table. A second end of the first actuator drive is connected to the base. Further, a second actuator drive has a first end connected to the patient table and a second end connected to the base. Finally, a third actuator drive has a first end connected to a common longitudinal position of the first actuator drive and a second end connected to the base.

14 Claims, 3 Drawing Sheets

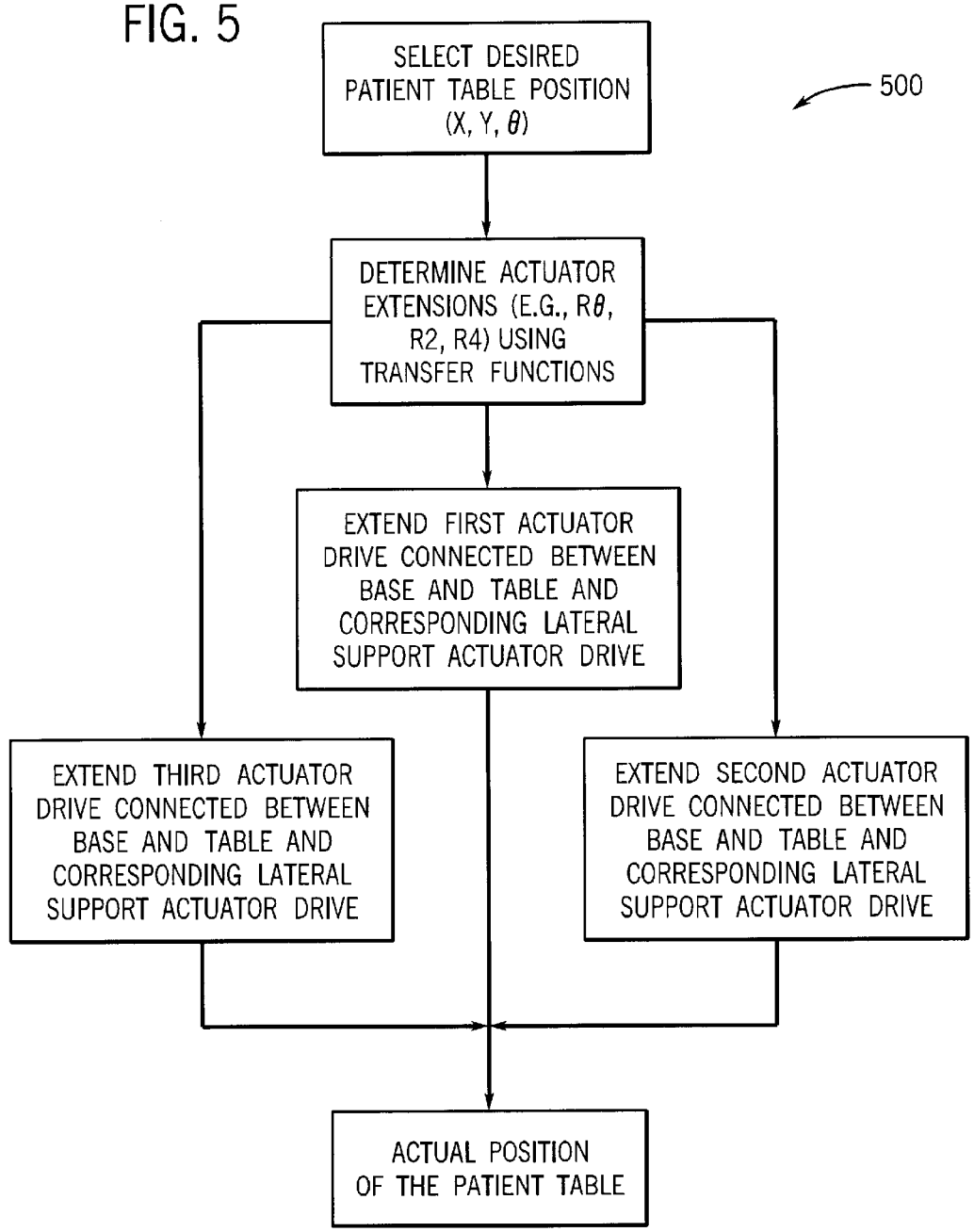

MULTI-AXIS PLANAR MECHANISM FOR A POSITIONER PATIENT PLATFORM

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

Positioner patient platforms allow a medical practitioner to properly position a patient during certain medical procedures, including, for example, XR, CT, Nuclear and PET procedures. Initially, these positioner platforms were little more than table-tops upon which a patient could lie. These prior patient platforms had only a limited ability to effect elevational changes in order to allow for the proper positioning of a patient. Moreover, these prior patient platforms did not allow for longitudinal changes to the location of the platform, and permitted tilting, if at all, only about a fixed point of rotation. Indeed, prior patient platforms provided motion only along a single degree of freedom and, therefore, significantly limited the ability of a medical practitioner to move a patient in other directions.

Past patient platforms, therefore, made it cumbersome and difficult, for example, for disabled or wheelchair-bound patients to gain initial access to the patient platform. In addition, past patient platforms unduly complicated the process of properly and accurately positioning the prone patient during a medical procedure. In particular, prior platforms did not permit independent or combined adjustments to elevation, tilt, or longitudinal position.

Beyond making it difficult to properly position a patient, prior patient platforms also limited a medical practitioner's access to the patient. Patient access, of course, is an important factor in achieving proper patient monitoring, positioning, and diagnosis. However, patient platforms permitting elevational changes, for example, were frequently designed in a "C" configuration, such that a supporting member interfered with access to the patient from at least one side of the platform.

A need has long existed for a new and improved positioner patient platform which overcomes the difficulties described above and others previously experienced.

SUMMARY OF THE INVENTION

In a preferred embodiment of the invention, a multi-axis positioner patient platform includes a patient table and a base. A first actuator drive having a first end connects to the patient table. A second end of the first actuator drive connects to the base. Further, a second actuator drive disposed longitudinally from the first actuator drive has a first end connected to the patient table and a second end connected to the base. Additionally, a third actuator drive is included and has a first end positioned at the same longitudinal position as the first end of the first actuator drive and a second end positioned at the same longitudinal position as the second end of the second actuator drive.

In an alternative embodiment of the invention, a multi-axis positioner patient platform includes a patient table and a base. A first actuator drive having a first end connects to the patient table. A second end of the first actuator drive connects to the base. Further, a second actuator drive, disposed substantially parallel to the first actuator drive, has a first end connected to the patient table and a second end connected to the base. Additionally, a third actuator drive is included and has a first end connected to the first actuator drive and a second end connected to the base.

The preferred embodiment has a number of advantages. The first, second, and third actuator drives can be independently extended to allow three degrees of independent motion. In particular, this configuration permits independent or combined adjustments to elevation, tilt, or longitudinal position. Other features and advantages of the invention will become apparent from the description that follows.

BRIEF DESCRIPTION OF THE DRAWINGS

Additional objects and features of the invention will appear from the following description in which the preferred embodiments are set forth in conjunction with the accompanying drawings.

FIG. 5 is a flowchart that illustrates a method for positioning a patient table.

DETAILED DESCRIPTION OF THE PREFERRED EMBODIMENT

Figure 1:
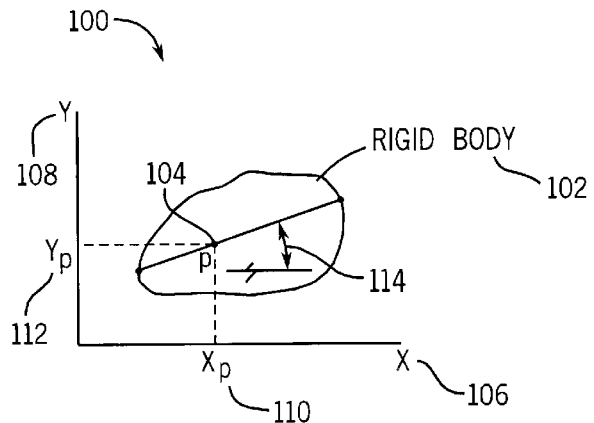
FIG. 1 illustrates a rigid body constrained to move with planar motion along three degrees of freedom.

Turning to FIG. 1, inertial coordinate system 100 shows a rigid body 102 with a point P. The inertial coordinate system has X-coordinate and Y-coordinate axes. Point P of the rigid body 102 is located at X-coordinate $X_p$ and Y-coordinate $Y_p$. The angle theta characterizes rotation of the rigid 102 body relative to the inertial coordinate system and is defined as a counterclockwise rotation about a Z-coordinate axis (not shown). The $X_p$ and $Y_p$ coordinates of the point P along with the angle ø or ("theta") form an independent set of three parameters describing the rigid body's position in the plane, as it moves with XY planar motion with three independent degrees of freedom (X, Y, theta). The X direction is generally referred to below as the longitudinal direction, the Y direction is generally referred to as the elevation direction, and theta represents tilt.

Figure 2:
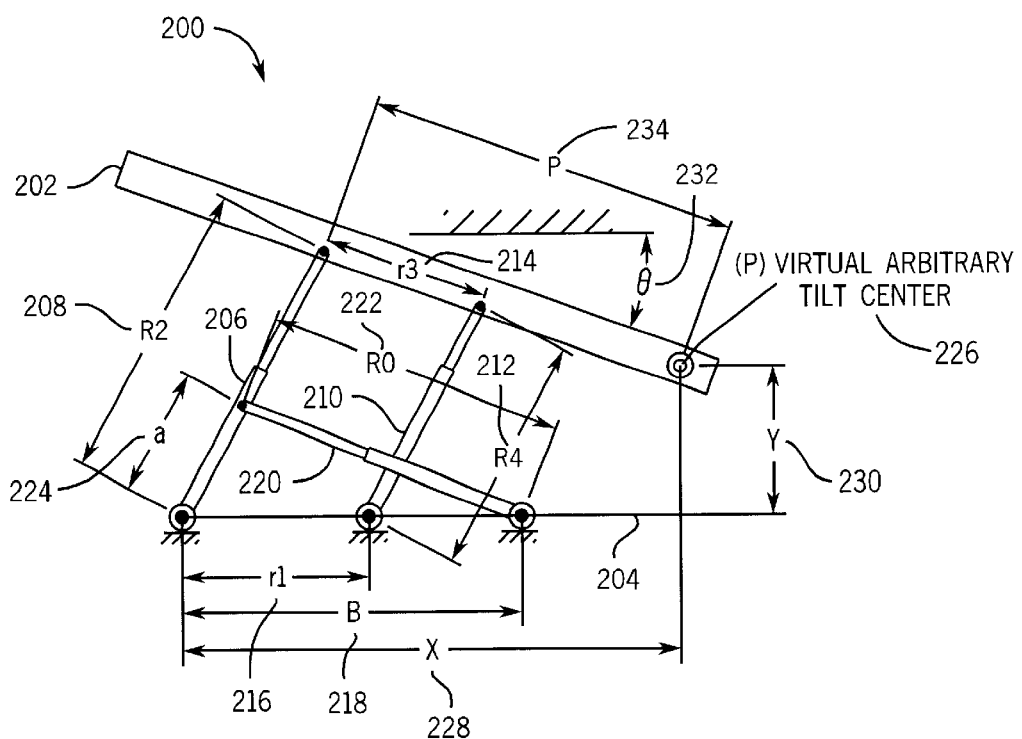
FIG. 2 is a side elevational view of one embodiment of a positioner patient platform.

Turning next to FIG. 2, one embodiment of the multi-axis global positioner patient platform 200 is illustrated. The multi-axis global positioner patient platform 200 includes a patient table 202 and a base 204. A first actuator drive 206 has a variable length R2. A second actuator drive 210 has a variable length R4. The first actuator drive 206 and the second actuator drive 210 are disposed a distance r3 from each other at the patient table 202, and a distance r1 at the base 204. A third actuator drive 220 has a variable length R0 and has one end 212 disposed at location "a" of the first actuator drive 206 and a second end 214 disposed at a distance B along the base 204. Distance B may be varied. A virtual arbitrary tilt center (P) is shown at coordinates X, Y, and theta, and is analogous to point P in FIG. 1 above. The virtual arbitrary tilt center (P) is located a distance P, along the patient table 202, from the first actuator drive 206.

The first actuator drive 206 connects to the base 204 and the patient table 202. The second actuator drive 210 is connected to the base 204 at location r1, and the patient table 202 at location r3. In the embodiment shown in FIG. 2, the second actuator drive 210 is substantially parallel to the first actuator drive 206. However, the second actuator drive 210 is not limited to such an orientation. Finally, the third actuator drive 220 is connected to the base 204 at location B at one end 214 and the first actuator drive 206 at location "a" at the other end 212. Movement of the patient table 202 in three independent degrees of freedom is effected by extending or contracting, in combination or independently, either the first actuator drive 206, the second actuator drive 210, or the third actuator drive 220. These changes permit independent or combined adjustments to the elevation (Y), tilt (theta), or longitudinal position (X) of the patient table 202.

The first actuator drive 206, the second actuator drive 210, and the third actuator drive 220 have their respective lengths R2, R4, and R0 controlled according to the following Transfer Functions:

$$R2 = \sqrt{(Y - P \cdot \sin(\theta))^2 + (X - P \cdot \cos(\theta))^2}$$

$$R4 = \sqrt{(Y + (r3 - P) \cdot \sin(\theta))^2 + ((X - r1) + (r3 - P) \cdot \cos(\theta))^2}$$

$$R0 = \sqrt{a^2 + B^2 - 2 \cdot a \cdot B \cdot \frac{(X - P \cdot \cos(\theta))}{\sqrt{(Y - P \cdot \sin(\theta))^2 + (X - P \cdot \cos(\theta))^2}}}$$

In other words, given a desired X, Y, and theta for the table 202, an associated control system may determine the R0, R2, and R4 actuator extensions from the transfer functions. The control system may then control the actuator drives 206, 210, and 220 to the determined R0, R2, and R4.

It is also noted that an additional degree of freedom, i.e., roll of the patient table, may be implemented through the use of single point connections to the patient table 202. In this alternative embodiment, the first actuator drive 206 is connected to the patient table 202 at one end 216 using a single point connection and is connected at a second end 208 to the base 204 by two points establishing an axis rotation. The second actuator drive 210 is divided into two separate actuator drives (R4, R5), each of which is connected to the patient table at one end 218 through a single point connection. The third actuator drive 220 is disposed as discussed above. By varying the length of the four actuator drives (R0, R2, R4, R5) connected to the patient table 202, an additional rolling degree of freedom can be achieved.

Figure 3:
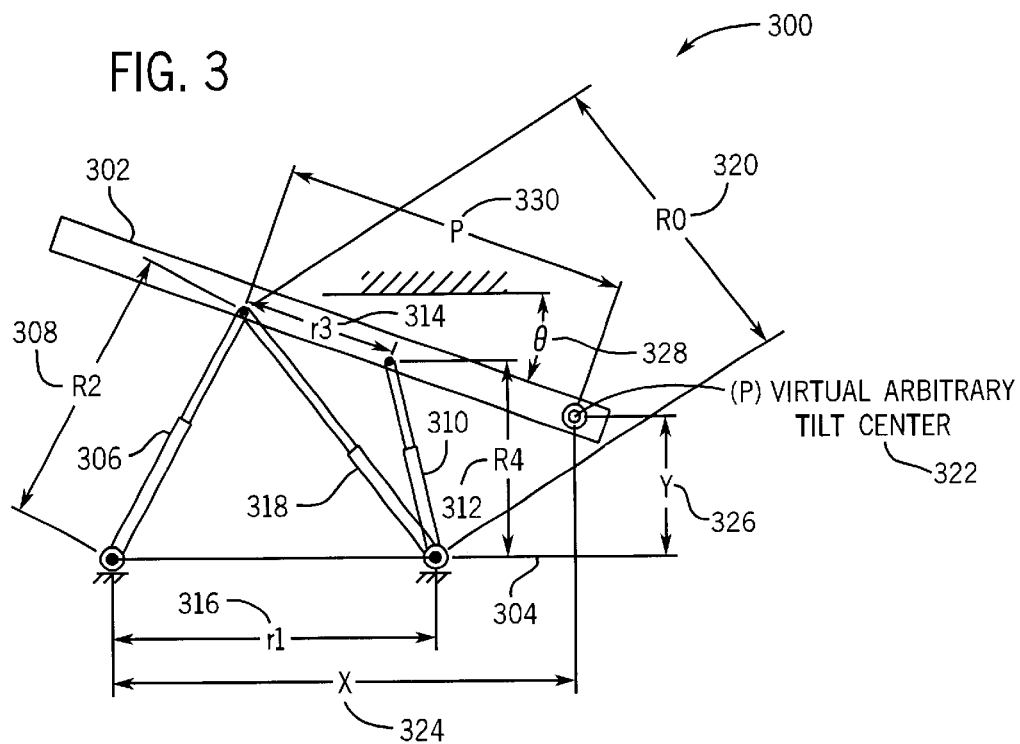
FIG. 3 is a side elevational view of an alternative embodiment of a positioner patient platform.

Turning now to FIG. 3, a preferred embodiment of a multi-axis global positioner patient platform 300 is illustrated. The multi-axis global positioner patient platform 300 includes a patient table 302 and a base 304. A first actuator drive 306 has a variable length R2. A second actuator drive has a variable length. The first actuator drive 306 and the second actuator drive 310 are disposed a distance r3 from each other at the patient table 302, and a distance r1 at the base 304. A third actuator drive 318 has a variable length R0 and is positioned at one end at approximately the same longitudinal position as a first end of the first actuator drive 308, and is positioned at the other end at approximately the same longitudinal position as the second end of the second actuator drive 312. A virtual arbitrary tilt center (P) is shown located at coordinates X, Y, and theta, and is analogous to point P in FIG. 1 above. The virtual arbitrary tilt center (P) is located a distance P, along the patient table 302, from the first actuator drive 306.

The first actuator drive 306 is connected to the base 304 and the patient table 302. The second actuator drive 310 is connected to the base 304 at location r1, and the patient table 302 at location r3. The third actuator drive 310 is connected to the base 304 at approximately the same longitudinal position as the second end of the second actuator drive 312, and at the other end is positioned at approximately the same longitudinal position as the first end of the first actuator drive 308. The virtual arbitrary tilt center (P) is located on the patient table 302. Movement of the patient table 302 in three independent degrees of freedom can be effected by extending or contracting, in combination or independently, either the first actuator drive 306, the second actuator drive 310, or the third actuator drive 318. These changes permit independent or combined adjustments to the elevation (Y), tilt (theta), or longitudinal position (X) of the patient table 302. The first actuator drive 306, the second actuator drive 310, and the third actuator drive 318 have their respective lengths R2, R4, and R0 controlled according to the following Transfer Functions:

$$R2 = \sqrt{(Y - P \cdot \sin(\theta))^2 + (X - P \cdot \cos(\theta))^2}$$

$$R4 = \sqrt{(Y + (r3 - P) \cdot \sin(\theta))^2 + ((X - r1) + (r3 - P) \cdot \cos(\theta))^2}$$

$$R0 = \sqrt{a^2 + B^2 - 2 \cdot a \cdot B \cdot \frac{(X - P \cdot \cos(\theta))}{\sqrt{(Y - P \cdot \sin(\theta))^2 + (X - P \cdot \cos(\theta))^2}}}$$

where B=r1 and a=R2.

Figure 4:
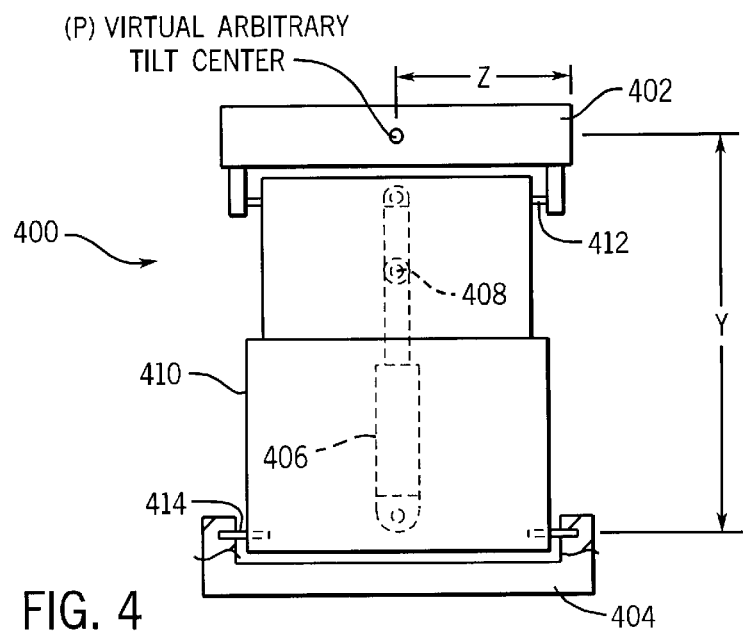
FIG. 4 is a front view of one embodiment of a positioner patient platform illustrating the location of the actuator drives and related support members.

Again, it is noted that an additional degree of freedom, i.e., roll of the patient table 302, may be achieved through the use of single point connections to the patient table 302. In this alternative embodiment, the first actuator drive 306 is connected to the patient table 302 at a single point connection 314. The second actuator drive 310 is divided into two separate actuator drives (R4, R5), each of which is connected to the patient table 302 through single point connections 316. The third actuator drive 318 is disposed as discussed above. By varying the length of the four actuator drives (R0, R2, R4, R5) connected to the patient table 202, an additional rolling degree of freedom can be achieved Turning now to FIG. 4, an exemplary embodiment of the multi-axis global positioner patient platform 400 is illustrated in frontal view. The multi-axis global positioner patient platform 400 includes a patient table 402, a base 404, a patient table pivot 412, and a base pivot 414. A first actuator drive 406 is shown disposed a distance Z from the end of the patient table 402. A third actuator drive 408 is positioned at one end to base 404 and to the first actuator drive 406 at the other end. The first actuator drive 406 is illustrated in FIG. 4 as being disposed within a support member 410 that provides for lateral stability of the patient table 402.

The first actuator drive 406 connects to the patient table 402 at one end 412 and the base 404 at another end 414. The support member 410 connects to the patient table 402 and the base 404 and provides for lateral stability of the patient table. The patient table 402 pivots about the patient table pivot 412 and the base pivot 414. The virtual arbitrary tilt center (P) is located a distance Z from the edge of the patient table 402.

Turning now to FIG. 5, a flowchart 500 illustrates a preferred embodiment of a method for positioning a patient table. The method comprises the first step of selecting a desired patient table position (X, Y, theta). The next step in the method of positioning the patient table involves determining the actuator extensions, e.g., R0, R2, R4, using the transfer functions. The next step in the method of positioning the patient table involves extending, if necessary, an end of a first actuator drive connected between the base and the patient table and the corresponding lateral support actuator drive. The next step in positioning the patient table involves extending, if necessary, a second actuator drive connected between the base and the table and the corresponding lateral support actuator drive. The next step in the method of positioning the patient table involves extending, if necessary, a third actuator drive connected between the base and the table and the corresponding lateral support actuator drive. The end of the first actuator drive and the end of the second actuator drive can be extended simultaneously, at different times, to different lengths, or at different rates to achieve rotational or elevational translation of the patient table. Similarly, the third actuator drive can be extended simultaneous with the first and second actuator drives, or at different times, to different lengths, or at different rates to achieve rotational or longitudinal translation of the patient table. By changing the actuator drive lengths, in one embodiment in accordance with the transfer functions described above, one method of practicing the invention is illustrated.

The present invention thereby provides a method and apparatus for positioning a patient table in multiple independent degrees of freedom. The positioning is achieved by changing the lengths of multiple actuator drives in accordance with predetermined transfer functions R0, R2, and R4. Prior limitations on patient access and limited range of motion of the patient table are eliminated.

While the invention has been described with reference to a preferred embodiment, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A multi-axis positioner patient platform comprising:
   a patient table comprising a patient supporting frame, the patient supporting frame being connected to a base only by three actuator drives, wherein
   a first actuator drive having a first end is directly connected to the patient supporting frame and a second end connected to the base;
   a second actuator drive having a first end is directly connected to the patient supporting frame and a second end connected to the base; and a third actuator drive having a first end is connected to the first actuator drive and a second end connected to the base.

2. The multi-axis positioner patient platform of claim 1 wherein the first end of the third actuator drive is positioned approximately at a common longitudinal position as the first end of the first actuator drive.

3. The multi-axis positioner patient platform of claim 2 wherein the second end of the third actuator drive and the second end of the second actuator drive are positioned at approximately a common longitudinal position.

4. The multi-axis positioner patient platform of claim 1 wherein the first, second, and third actuator drives are selected from the group of mechanical, hydraulic, and pneumatic actuators.

5. The multi-axis positioner patient platform of claim 1 wherein the first, second, and third actuator drives are each disposed within a support member providing lateral stability.

6. A multi-axis positioner patient platform comprising:
   a patient table comprising a patient supporting frame, the patient supporting frame being connected to a base only by three actuator drives, wherein
   a first actuator drive having a first end is directly connected to the patient supporting frame and a second end connected to the base;
   a second actuator drive having a first end is directly connected to the patient supporting frame and a second end connected to the base; and
   a third actuator drive having a first end is positioned at approximately the same longitudinal position as the first end of the first actuator drive and a second end positioned at approximately the same longitudinal position as the second end of the second actuator drive.

7. The multi-axis positioner patient platform of claim 6 wherein the first end of the third actuator drive is connected to the first end of the first actuator drive.

8. The multi-axis positioner patient platform of claim 6 wherein the first, second, and third actuator drives are selected from the group of mechanical, hydraulic, and pneumatic actuators.

9. The multi-axis positioner patient platform of claim 6 wherein the first, second, and third actuator drives are each disposed within a support member providing lateral stability.

10. A method of positioning a patient table comprising a patient supporting frame, the patient supporting frame being connected to a base only by three actuator drives the method comprising the steps of:
    extending an end of a first actuator drive directly connected to the patient supporting frame and the base to a first extension;
    extending an end of a second actuator drive directly connected to the patient supporting frame and the base to a second extension; and
    extending an end of a third actuator drive connected to the first actuator drive to a third extension.

11. The method of claim 10 wherein the end of the first actuator drive and the end of the second actuator drive are extended at the same time to provide rotation or elevational translation of the patient supporting frame.

12. The method of claim 11 wherein the end of the third actuator drive is extended at the same time to provide rotation or longitudinal translation of the patient supporting frame.

13. The method of claim 11 further comprising the step of selecting a desired position(X, Y, theta) to which to move the patient supporting frame.

14. The method of claim 13 further comprising the step of determining the first, second, and third extensions according to at least one transfer function.

* * * * *